(12) United States Patent
Masella et al.

(10) Patent No.: US 8,474,461 B2
(45) Date of Patent: Jul. 2, 2013

(54) APPARATUS FOR HOLDING NASAL TUBES

(76) Inventors: Stephen J. Masella, Wallingford, CT (US); Deborah L. Masella, Wallingford, CT (US)

( * ) Notice: Subject to any disclaimer, the term of this patent is extended or adjusted under 35 U.S.C. 154(b) by 951 days.

(21) Appl. No.: 11/528,806

(22) Filed: Sep. 28, 2006

(65) Prior Publication Data
US 2007/0289597 A1 Dec. 20, 2007

Related U.S. Application Data

(60) Provisional application No. 60/814,128, filed on Jun. 17, 2006.

(51) Int. Cl.
*A61M 15/08* (2006.01)

(52) U.S. Cl.
USPC ............. 128/207.18; 128/206.11; 128/207.11

(58) Field of Classification Search
USPC ............. 128/206.11, 206.18, 206.28, 207.11, 128/207.13, 207.17, 207.18; 604/174, 180
See application file for complete search history.

(56) References Cited

U.S. PATENT DOCUMENTS

| | | | | |
|---|---|---|---|---|
| 2,168,705 A | * | 8/1939 | Francisco et al. | 128/207.18 |
| 2,590,006 A | * | 3/1952 | Gordon | 604/180 |
| 3,046,989 A | | 7/1962 | Hill | 128/348 |
| 4,120,304 A | | 10/1978 | Moor | 128/348 |
| 4,122,857 A | * | 10/1978 | Haerr | 604/180 |
| 4,282,871 A | | 8/1981 | Chodorow et al. | 128/207.18 |
| 4,284,076 A | | 8/1981 | Hall | 128/207.18 |
| D260,932 S | | 9/1981 | Chodorow et al. | D24/53 |
| D261,680 S | | 11/1981 | Hall | D24/53 |
| 4,645,492 A | | 2/1987 | Weeks | 604/174 |
| 4,658,813 A | | 4/1987 | Jones | 128/207.14 |
| 4,702,736 A | | 10/1987 | Kalt et al. | 604/180 |
| 4,738,662 A | | 4/1988 | Kalt et al. | 604/180 |
| 4,804,374 A | | 2/1989 | Laskody | 604/180 |
| 4,823,789 A | | 4/1989 | Beisang, III | 128/207.18 |
| 4,838,878 A | | 6/1989 | Kalt et al. | 604/180 |
| 4,852,189 A | * | 8/1989 | Duggan | 2/452 |
| 4,932,943 A | | 6/1990 | Nowak | 604/180 |
| 4,986,815 A | | 1/1991 | Schneider | 604/180 |
| 5,076,269 A | | 12/1991 | Austin | 128/207.17 |
| 5,134,995 A | | 8/1992 | Gruenke et al. | 128/204.23 |
| 5,156,641 A | | 10/1992 | White | 128/207.18 |
| 5,172,688 A | | 12/1992 | Dillon | 128/207.18 |
| 5,259,373 A | | 11/1993 | Gruenke et al. | 128/204.23 |
| 5,474,060 A | | 12/1995 | Evans | 128/204.22 |
| 5,549,106 A | | 8/1996 | Gruenke et al. | 128/204.23 |
| 5,558,090 A | * | 9/1996 | James | 128/207.18 |
| 5,595,174 A | | 1/1997 | Gwaltney | 128/201.15 |
| 5,687,715 A | * | 11/1997 | Landis et al. | 128/207.18 |
| 5,794,614 A | | 8/1998 | Gruenke et al. | 128/204.21 |
| 5,833,663 A | | 11/1998 | Bierman et al. | 604/174 |
| 5,845,636 A | | 12/1998 | Gruenke et al. | 128/204.23 |
| 6,093,169 A | * | 7/2000 | Cardoso | 604/94.01 |
| 6,655,384 B2 | | 12/2003 | Antenbring et al. | 128/207.14 |
| 6,854,465 B2 | * | 2/2005 | Bordewick et al. | 128/207.11 |

(Continued)

*Primary Examiner* — Quang D Thanh
(74) *Attorney, Agent, or Firm* — Robert M. Amici

(57) ABSTRACT

The present invention relates to a nasal tube holder having a conformable body with a nose section and a forehead section. At least one nasal tube inserted into a patient's nose is held to the conformable body, and the conformable body is held to a patient's forehead. Also disclosed is a method for securing at least one nasal tube to a patient's nose and forehead.

13 Claims, 5 Drawing Sheets

U.S. PATENT DOCUMENTS

| | | | | |
|---|---|---|---|---|
| 7,156,097 B2* | 1/2007 | Cardoso | | 128/206.11 |
| 2001/0029954 A1* | 10/2001 | Palmer | | 128/207.17 |
| 2003/0034030 A1* | 2/2003 | Carlucci et al. | | 128/200.24 |
| 2003/0172936 A1* | 9/2003 | Wilkie et al. | | 128/207.18 |
| 2004/0045553 A1* | 3/2004 | Cardoso | | 128/207.18 |
| 2006/0081250 A1* | 4/2006 | Bordewick et al. | | 128/206.11 |

* cited by examiner

FIG 1A        FIG 1B

APPARATUS FOR HOLDING NASAL TUBES

CROSS REFERENCE TO RELATED APPLICATIONS

This application claims the benefit of U.S. Provisional Patent Application No. 60/814,128, filed Jun. 17, 2006.

BACKGROUND OF THE INVENTION

1. Field of the Invention

The present invention relates to medical devices capable of holding nasal tubes in place.

2. Description of the Related Art

Medical tubes are often used to provide an unobstructed pathway into a patient. For example, a naso-gastric tube is inserted into the patient's nose down the esophagus and into the stomach to provide a method of feeding the patient, delivering medication, or keeping the stomach decompressed. A naso-jejunum tube, which is inserted in a similar manner through the stomach and into the patient's jejunum, enables the patient to be fed directly into their intestines. These tubes are often mercury weighted in order to be monitored radiologically for proper insertion depth.

Nasal tubes are often inserted and left in place for an extended period of time. Movement by the patient during sleep or under other circumstances, such as coming out of anesthesia, sometimes causes the tubes to move out of position. Also, small children, particularly those that are mentally challenged, may not understand the importance of the tubes and may attempt to pull them out. However, unlike other types of tubes, such as those used for respiration, repositioning of nasal tubes can be extremely time consuming and medically stressful on the patient. For this reason, nasal tubes must be securely fastened to the patient in order to ensure that they are not inadvertently removed or disturbed.

A variety of techniques are known for securing nasal tubes. For example, adhesive tape can be used to attach the tube to the patient's face. However, movement of the tube could cause tearing or detachment of the tape, and constant replacement with new tape can cause skin irritation. Also, securing the tubing with tape to the patient's cheek often results in indentations on their skin from the tubing that can lead to skin breakdown. Furthermore, many patients requiring nasal tubes are malnourished, which can substantially compromise their integumentary system, making them more susceptible to skin breakdown with a decreased ability for recovery.

Furthermore, several devices have been described for this purpose. For example, U.S. Pat. Nos. 3,046,989, 5,172,688, and 5,833,663 describe a flexible or moldable nose piece that includes a mechanism for holding a tube underneath a patient's nose. U.S. Pat. Nos. 4,120,304, 4,932,943, and 4,986,815 also describe strips that fit over the patient's nose and include a clamping type device to secure the tube. However, for each of these, the nasal tube inserted into the patient remains under the nose, which would partially obstruct the patient's mouth. Since some patients also require medical tubing inserting either into the mouth (such as an endotracheal tube) or, for respiratory conditions, placed under the nose, obstruction by the nasal tube would be an issue. Furthermore, nasal tubes under the nose would be more easily dislodged or moved by a patient.

U.S. Pat. No. 4,702,736 describes a universal clamp that can be used for securing a nasal tube to a patient's forehead. Also, related U.S. Pat. Nos. 4,338,663, and 4,838,878 further describe the use of a nosepiece in conjunction with the universal claim. However, such a two-piece system would be complicated to use and would require alignment of the individual parts by medical staff.

Therefore, there is a need for a simple, comfortable, one piece apparatus that would be capable of securely fastening nasal tubes to a patient without the problems described above.

SUMMARY OF THE INVENTION

The present invention relates to a nasal tube holder comprising a conformable body having a nose section and a forehead section, at least one means for holding at least one nasal tube inserted into a patient's nose to the conformable body; and at least one means for holding the conformable body to a patient's forehead.

The present invention further relates to a method for securing at least one nasal tube to a patient's nose and forehead comprising, in any order, the steps of inserting at least one nasal tube into the patient, substantially conforming a conformable body to the patient's nose and forehead, attaching the nasal tube to the conformable body, and attaching the conformable body to the patient's forehead.

It is to be understood that both the foregoing general description and the following detailed description are exemplary and explanatory only and are intended to provide further explanation of the present invention, as claimed.

DETAILED DESCRIPTION OF THE INVENTION

Figure 1:
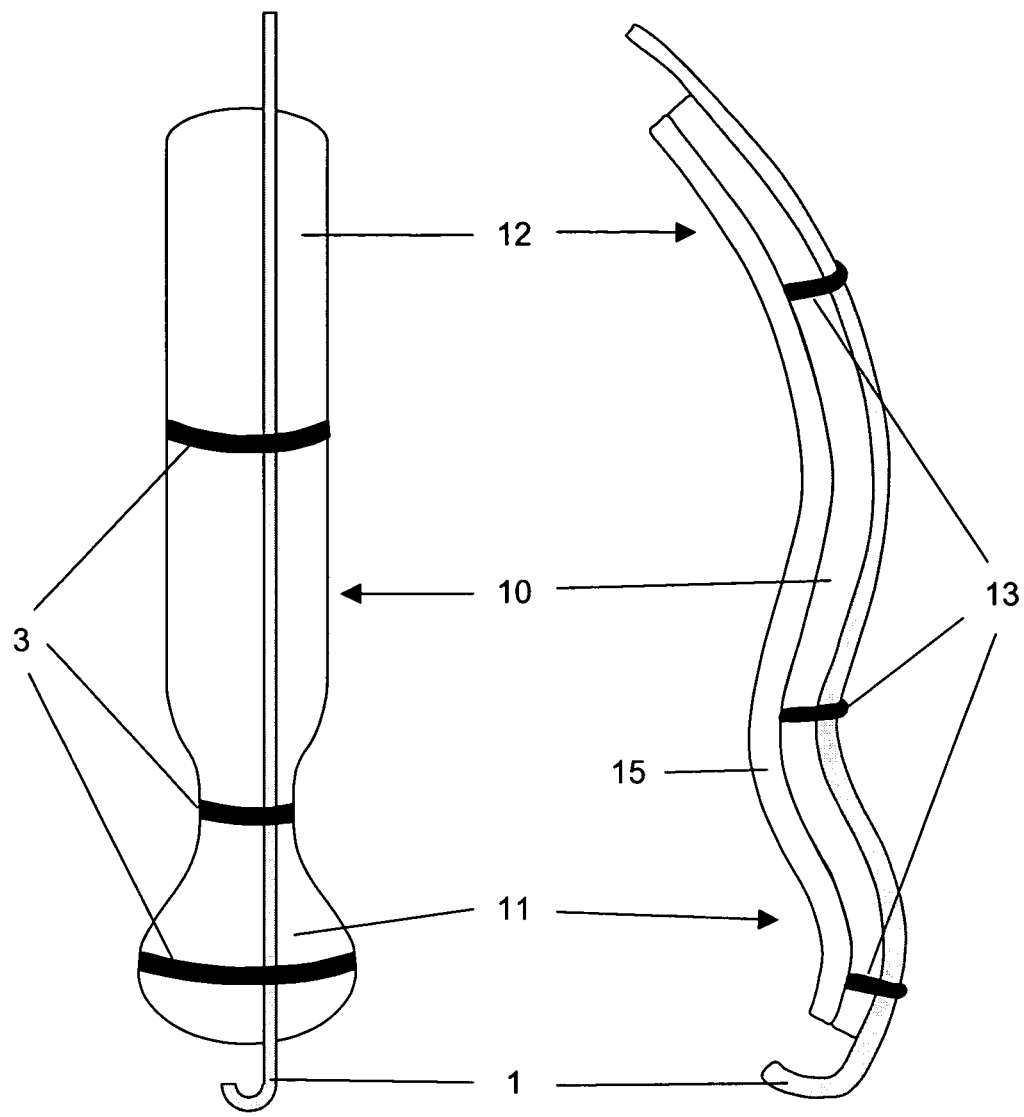
FIG. 1A and FIG. 1B are front and side views, respectively, of one embodiment of the nasal tube holder of the present invention.

The present invention relates to devices for securing medical tubes to a patient, particularly nasal tubes.

The nasal tube holder of the present invention comprises a conformable body having a nose section and a forehead section. By "conformable" is meant that this nasal tube holder is moldable to the shape and profile of the patient's nose and forehead. Thus, the conformable body may be flat but can be bent or molded along its length and/or width as needed to substantially conform to the patient, thereby providing the greatest fit and maximum comfort. Suitable conformable materials include flexible or pliable metals such as aluminum or copper and various plastics, particularly those that can be formed or bent at temperatures above room temperature but which are solid or non-conformable at room temperature. The conformable body should also be thin in order to provide maximum conformability and minimal bulk and weight but thick enough to provide sufficient rigidity. Preferably the conformable body has a thickness less than or equal to 5 mm and more preferably less than or equal to 2 mm and a width of less than about 4 cm, preferably less than about 3 cm, and more preferably less than about 2 cm.

The surface of the conformable body can also be smooth or polished in order to provide increased comfort and protection.

Also, the surface of the conformable material may be coated with a thin layer of material, such as a soft plastic coating. Such coatings are preferably used when the conformable body is a flexible metal, thereby protecting the metal and the patient.

The conformable body has a length that extends from the patient's nose to the patient's forehead, preferably to the hairline. For example, the length of the conformable body may be between about 5 cm and about 25 cm long, preferably between about 5 cm and about 20 cm long, and more preferably between about 8 cm and about 15 cm long. Preferably, the length is adjustable in order to provide a more universal fit to suit the needs of both younger or smaller patients as well as adults. A variety of different means for adjusting the length of the conformable body may be used. For example, the conformable body may comprise two overlapping sections where the amount of overlap is varied in order to adjust the overall length of the conformable body. One of the overlapping sections may comprise an attachment means, such as at least one snap or button, and the other overlapping section may comprise various attachment sites to which these attachment means can be attached. By attaching one overlapping section to the other at different locations, the length of the conformable body can be adjusted. In addition, the conformable body may comprise two sections wherein one section can be inserted into or over the second section, allowing the sections to slide relative to each other. The sliding sections may further comprise a means for locking the sliding sections in place after the adjustment is made. Other known means of adjustment can also be used.

As described above, the conformable body comprises a nose section and a forehead section that are connected to each other. The nose section is placed over the nose of the patient, and preferably does not require any means of attachment to the patient. However, the nose section preferably further comprises at least one means for attaching the nasal tube to the conformable body, which is described in more detail below. The nose section generally has a shape, a length, and/or a width substantially similar to the patient's nose. For example, the nose section may be rounded or spoon-shaped in order to fit securely over the tip of the nose. Moreover, the nose section may further comprise at least one wing or tab along both sides that is bent or curved downward relative to the plane of the nose section in order to fit around the nose of the patient. Alternatively, the nose section may be flat, preferably including at least one wing or tab, and can be conformed to fit the curve of the patient's nose. The nose section may also comprise at least one flexible or soft pad attached to the side of the conformable body to be in contact with the patient, for added comfort and increased stability. Any pad known in the art can be used, including foam or cotton.

The forehead section of the conformable body is placed onto the patient's forehead and preferably further comprises at least one means for attaching the conformable body to the patient, which is discussed in more detail below. The forehead section may further comprise at least one protective pad attached to the side to be in contact with the patient. This protective pad may be any of those known in the art, including gauze or foam, that are capable of protecting the skin against abrasion. In particular, the protective pad may be one that is also capable of absorbing moisture, such as sweat. Alternatively, the forehead section may further comprise an adhesive layer attached to the side in contact with the patient. This can be used as a means for attaching the conformable body to the patient's forehead.

Thus, the nasal tube holder of the present invention further comprises at least one means for holding the conformable body to the patient's forehead. Preferably this is the only means for securing the device to the patient, and, more preferably, the forehead section of the conformable body comprises this means. A variety of different means can be used. For example, if the forehead section comprises an adhesive layer, as discussed above, a protective pad can be attached to the patient's forehead, to which the adhesive layer would then be capable of adhering. As a specific example of this, a protective pad, such as Tegasorb, may be placed on the patient's forehead, and a Velcro-type material may be adhered to the forehead section of the conformable body, enabling the present device to be secured to the patient.

As another example, the forehead section may further comprise a gauze headband, preferably attached to this section of the conformable body, which could be slipped over the patient's head. Alternatively, straps attached to the forehead section may be used that can be joined together to secure the nasal tube holder to the patient. For example, a strap can be attached to one side of the forehead section, which can wrap around the patient's head and be joined to the other side of the forehead section. Also, two straps may be used, each attached to opposite sides of the forehead section, that can each be wrapped around the patient's head and joined together at the back using, for example, a buckle, snap, or removable or adhesive strip, such as Velcro. These two straps may also be inserted into slots on opposite edges of the forehead section. Also, a third strap may be used attached to the top of the forehead section of the conformable body, or inserted into a slot located there, that can be wrapped over the patient's head and joined to the other straps at the back. Such a third strap has been found to provide improved stability against slipping and twisting, particular as the patient sleeps. For each of these examples, the straps or headband can be adjustable to provide a more universal fit and means of attaching the conformable body to the forehead.

The nasal tube holder of the present invention further comprises at least one means for holding at least one nasal tube to the conformable body. This means is also capable of holding multiple nasal tubes. Examples of nasal tubes include nasogastric tube (NG tubes), naso-jejunum tubes (NJ tubes), and nasal canula. Preferably, the nasal tube holder comprises multiple means for holding the nasal tube to the conformable body, such as two, three, or four means. These means can be on the nose section, the forehead section, or both sections of the conformable body. Preferably, the nose section comprises at least one and preferably two or more means for holding the nasal tubes, thereby providing better stabilization of the tubes as they exit the patient's nose. Even greater stabilization and security can be provided when the forehead section also comprises at least one means for holding the nasal tube. Thus, the means for holding the nasal tubes can be spread along the length of the conformable body, including the nose section and forehead section. Suitable means for holding the nasal tube include, for example, removable or adhesive bands, such as Velcro straps, or elastic bands or ties. Also, the means for holding the conformable body to the patient's forehead may also hold the nasal tubes to the forehead section of the conformable body.

The nasal tube holder of the present invention may further comprise at least one cover for the nasal tubes, in order to provide increased protection of the tubes and the means for holding the tubes to the conformable body. The cover, which may snap in place or otherwise be secured to the conformable body, can be on the nose section, the forehead section, or both.

The nasal tube holder of the present invention may further comprise one or more markings to visually confirm that one or more of the nasal tubes have not inadvertently moved. Such markings typically coincide with a mark located on the tubes themselves. For example, the marking may be a simple line stamped or etched into the conformable body or may be a measuring device, such as a portion of a ruler, incorporated onto the conformable body, such as along the edge.

Specific embodiments of the present invention are shown in FIG. 1A, FIG. 1B, FIG. 2, FIG. 3, FIG. 4A, FIG. 4B, and FIG. 5. These figures are meant to further clarify the present invention and are intended to be only exemplary in nature.

Figure 2:
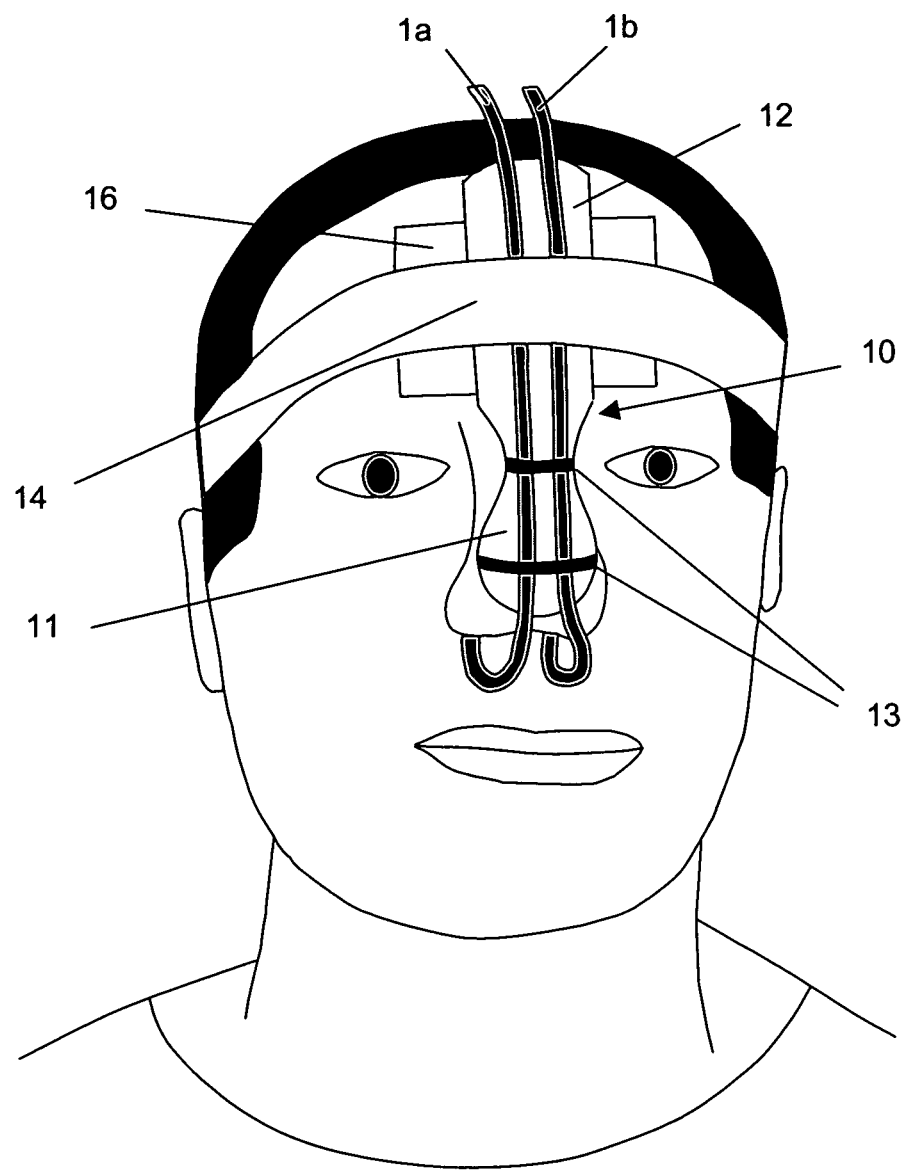
FIG. 2 shows one embodiment of the nasal tube holder of the present invention on a patient.

FIG. 1A and FIG. 1B are front and side views, respectively, of one embodiment of the nasal tube holder of the present invention. This nasal tube holder comprises a conformable body 10 having a nose section 11 and a forehead section 12. As can be seen in both figures, nose section 11 has a rounded shape to substantial conform to the nose of a patient. Also, as can be seen in FIG. 1B, conformable body 10 has already been conformed to the shape of a facial profile. This is also true for the embodiments shown in the figures that follow FIG. 1A and FIG. 1B. The nasal tube holder further comprises at least one means 13 for holding a nasal tube 1 to conformable body 10 (three bands are shown). Means for holding conformable body 10 to the forehead of a patient is shown in FIG. 2. For this embodiment, conformable body 10 further comprises a flexible pad 15 attached to the back (the side to be in contact with a patient) in order to provide improved comfort and better fit.

Figure 3:
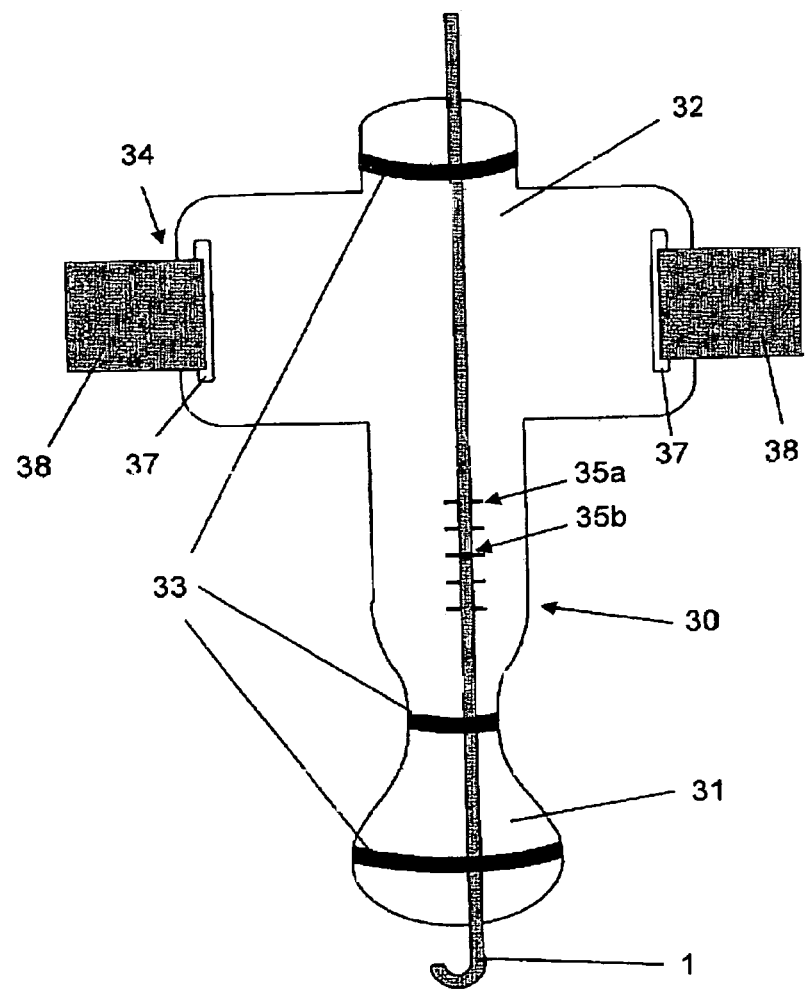
FIG. 3 is a front view of another embodiment of the nasal tube holder of the present invention.

In FIG. 3, another embodiment of the nasal tube holder of the present invention is shown. This nasal tube holder comprises a conformable body 30, having a nose section 31 and forehead section 32, means 33 for holding nasal tube 1 to conformable body 30 (three bands are shown), and means 34 for holding conformable body 30 to a patient's forehead. Means 34 includes two slots 37 on either side of forehead section 32, and, inserted into each slot 37 is a strap 38, which would wrap around the patient's head and be secured there, by, for examples, a buckle; a snap, or a removable or adhesive strip. FIG. 3 also shows markings 35a provided on the nasal tube holder that coincide with mark 35b on tube 1.

In FIG. 3, another embodiment of the nasal tube holder of the present invention is shown. This nasal tube holder comprises a conformable body 30, having a nose section 31 and forehead section 32, means 33 for holding nasal tube 1 to conformable body 30 (three bands are shown), and means 34 for holding conformable body 30 to a patient's forehead. Means 34 includes two slots 37 on either side of forehead section 32, and, inserted into each slot 37 is a strap 38, which would wrap around the patient's head and be secured there, by, for examples, a buckle, a snap, or a removable or adhesive strip.

Figures 4A, 4B:
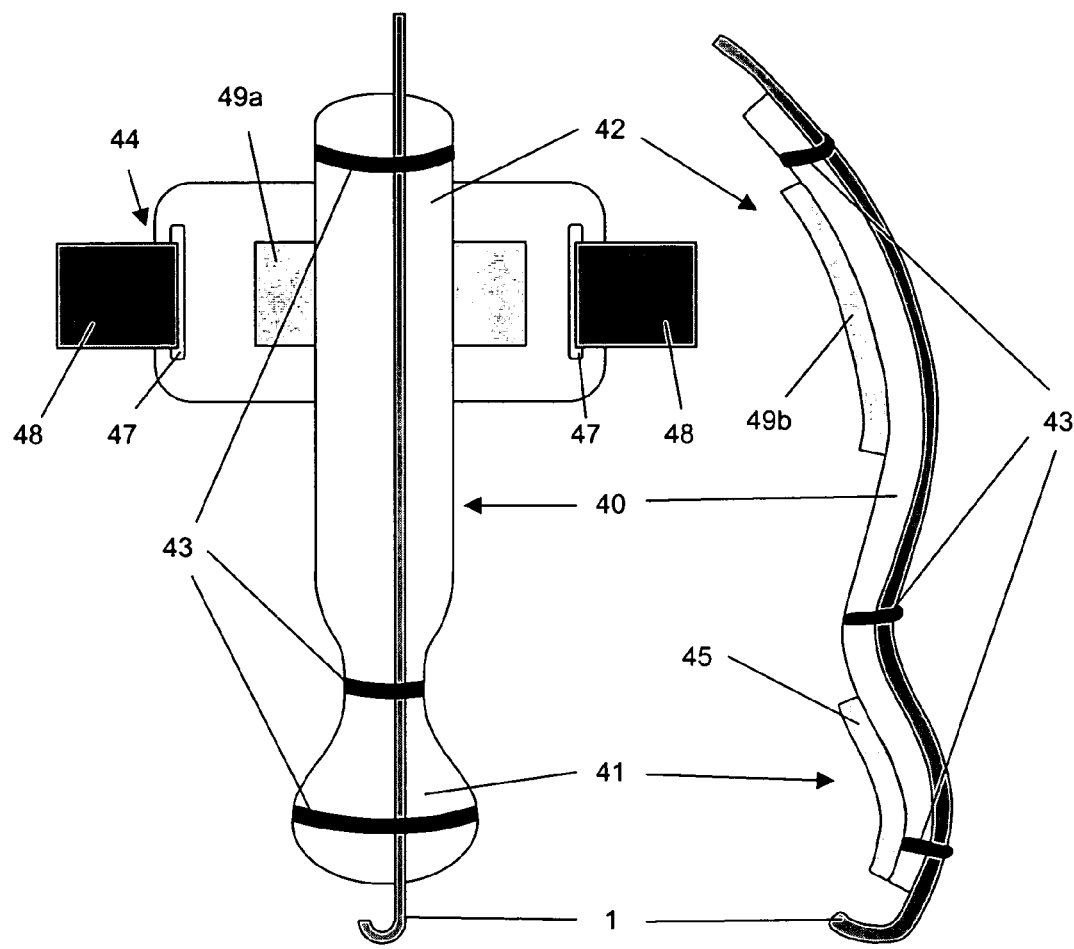
FIG. 4A and FIG. 4B are front and side views, respectively, of another embodiment of the nasal tube holder of the present invention.
Figure 5:
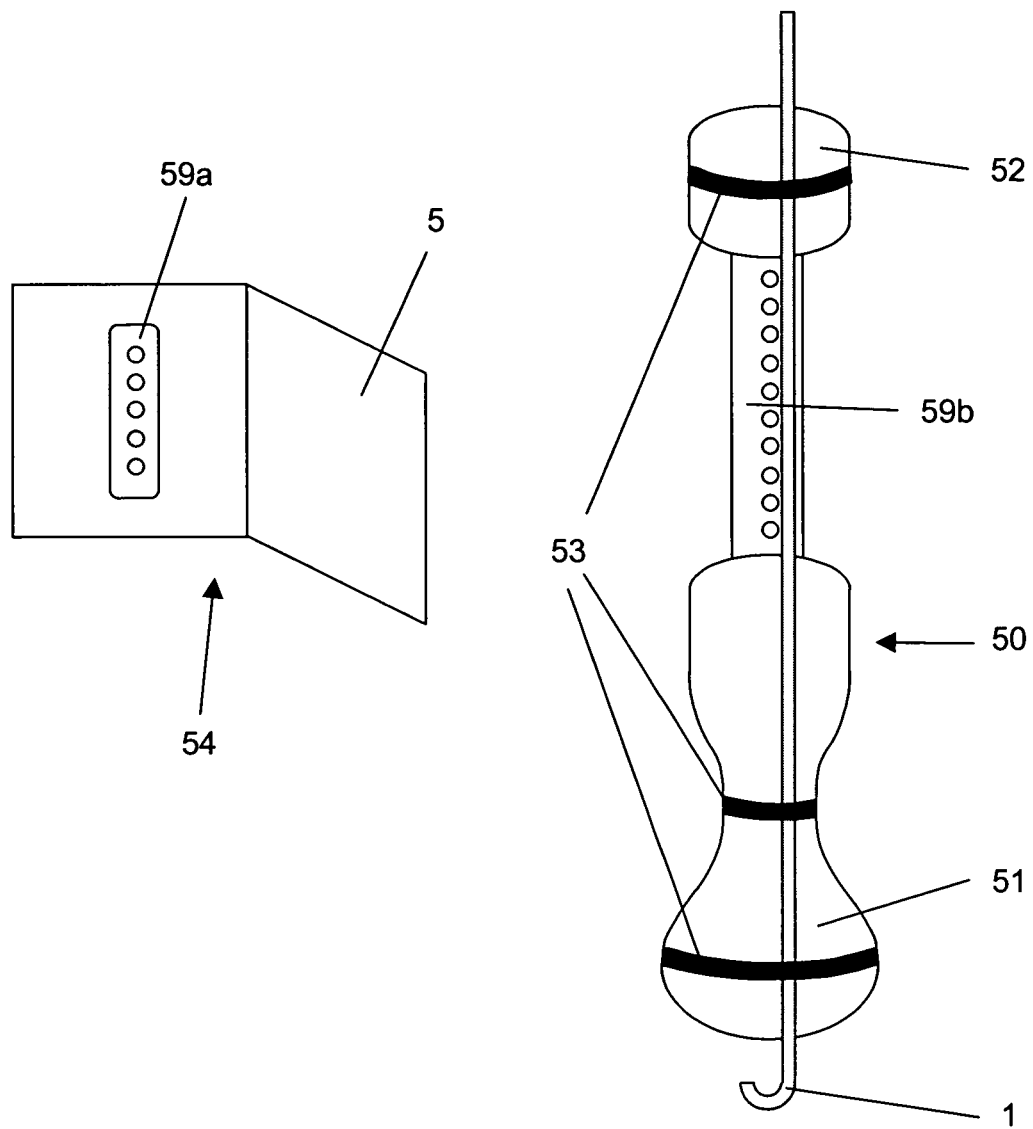
FIG. 5 is a front view of another embodiment of the nasal tube holder of the present invention.

FIG. 4A, FIG. 4B, and FIG. 5 each show an embodiment of the nasal tube holder of the present invention in which the length of the nasal tube holder can be adjusted.

Thus, in FIG. 4A and FIG. 4B, the nasal tube holder comprises a conformable body 40, having a nose section 41 and a forehead section 42, a means 43 for holding nasal tube 1 to conformable body 40 (three bands are shown), and a means 44 for holding conformable body 40 to a patient's forehead. Also included is a flexible pad 45 behind nose section 41. Means 44 includes two slots, 47 on either side of forehead section 42, and, inserted into each slot 47 is a strap 48. Also, means 44 includes a removable or adhesive strip 49a, such as Velcro. As shown in FIG. 4B, conformable body 40 also includes a matching removable or adhesive strip 49b, which has a length greater than the width of strip 49a. Thus, when means 44 is worn by an adult patient, conformable body 40 can be placed on means 44, attaching pads 49a and 49b at a location to match the length from the patient's nose to their forehead. When means 44 is worn by a smaller patient, such as a child, conformable body 40 can also be placed on means 44, attaching pads 49a and 49b at a different location suitable for that patient's profile.

In FIG. 5, the nasal tube holder comprises a conformable body 50, having a nose section 51 and a forehead section 52, a means 53 for holding nasal tube 1 to conformable body 50 (three bands are shown), and a means 54 for holding conformable body 50 to a patient's forehead. Also included is a flexible pad 55 behind nose section 51. Means 54 includes an overlapping section 59a while conformable body 50 comprises a matching overlapping section 59b. Thus, for this embodiment, nose section 51 and forehead section 52 are joined by overlapping section 59b. As shown in FIG. 5, overlapping section 59a contains small cylindrical posts (shown as darkened circles) while overlapping section 59b contains small holes (shown as open circles) into which these posts can be inserted. When means 54 is attached to the forehead of an adult patient, such as with an adhesive, conformable body 50 can be placed on means 54, with the posts of overlapping section 59a fitting into the holes of overlapping section 59b, thereby holding conformable body 50 to the patient. When means 54 is attached to the forehead of a smaller patient, such as a child, overlapping section 59b of conformable body 50 can be place on overlapping section 59a of means 54 at a different location suitable for that patient. Since conformable body 54 contains only one-piece, no alignment of separate nose and forehead sections is needed. Means 54 further comprises a cover 5 to further secure conformable body 50 and nasal tube 1 to the patient.

In addition, in another embodiment, the conformable body itself may comprise this type of overlapping section, with one of the overlapping sections being attached to the forehead section and the other overlapping section being attached to the nose section. Thus the conformable body would be in two parts, but could still be conformed to the shape of a patient's face. By inserting one overlapping section into the other at various locations, the length of the nasal tube holder can be adjusted. A means for holding this device, such as a headband, would also be used.

The present invention further relates to a method for securing at least one nasal tube to a patient's nose and forehead. This method comprises the steps of inserting at least one nasal tube into the patient and attaching the nasal tube holder of the present invention to the patient. Thus, the conformable body of the nasal tube holder of the present invention is substantially conformed to the patient's nose and forehead, the nasal tube or tubes are attached to the conformable body, and the conformable body is attached to the patient's forehead. These steps can occur in any order. For example, alternatively, the nasal tube or tubes can be attached to the nasal tube holder of the present invention prior to placing the device on the patient. Then, the conformable body can be molded or formed to fit the patient and finally secured to the patient's forehead.

It has been found that, by using this method and the nasal tube holder of the present invention, the nasal tubes can be kept off of the patient's face, maintaining unobstructed access to the nose and mouth and placing the tubes out of the way, thereby avoiding inadvertent moving or dislodging of the tubes. Also, this method and the nasal tube holder of the present invention do not require the use of adhesives to keep the nasal tubes secure, thereby avoiding the need for changing or repositioning the adhesives, which can cause significant skin breakdown and irritation.

The foregoing description of preferred embodiments of the present invention has been presented for the purposes of illustration and description. It is not intended to be exhaustive or to limit the invention to the precise form disclosed. Modifications and variations are possible in light of the above teachings, or may be acquired from practice of the invention. The embodiments were chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A naso-gastric or naso-jejunum tube holder comprising:
   a) a conformable body having an adjustable length comprising a nose section having an overlapping section and a forehead section comprising an overlapping section, wherein the overlapping section of the nose section is connectable at varying locations along the overlapping section of the forehead section, and wherein the conformable body thereby substantially conforms to a patient's nose and forehead and extending from the patient's forehead ending at a tip of the patient's nose,
   b) at least one means for holding at least one naso-gastric or naso-jejunum tube inserted into the patient's nose on a top of the nose section of the conformable body, the naso-gastric or naso-jejunum tube thereby substantially conforming to the top of the nose section of the conformable body along its entire length; and
   c) at least one means for holding the conformable body to the patient's forehead.

2. The naso-gastric or naso-jejunum tube holder of claim 1, wherein the naso-gastric or naso-jejunum tube holder comprises one or more markings that coincide with a mark located on the naso-gastric or naso-jejunum tube.

3. The naso-gastric or naso-jejunum tube holder of claim 1, comprising at least two means for holding the naso-gastric or naso-jejunum tube to the conformable body.

4. The naso-gastric or naso-jejunum tube holder of claim 3, wherein the nose section and the forehead section each comprise at least one of the at least two means for holding the naso-gastric or naso-jejunum tube.

5. The naso-gastric or naso-jejunum tube holder of claim 4, wherein the nose section comprises the at least two means for holding the naso-gastric or naso-jejunum tube.

6. The naso-gastric or naso-jejunum tube holder of claim 1, wherein the nose section further comprises at least one flexible pad adapted to be attached between the nose section and the patient's nose.

7. The naso-gastric or naso-jejunum tube holder of claim 1, wherein the means for holding the conformable body to the patient's forehead is a gauze headband attached to the forehead section.

8. The naso-gastric or naso-jejunum tube holder of claim 1, wherein the forehead section further comprises at least two slots and wherein the means for holding the conformable body to the patient's forehead is an adjustable strap inserted through the two slots.

9. The naso-gastric or naso-jejunum tube holder of claim 1, wherein the forehead section further comprises at least one protective pad adapted to be attached between the forehead section and the patient's forehead.

10. The naso-gastric or naso-jejunum tube holder of claim 1, wherein the conformable body is a flexible metal or plastic.

11. The naso-gastric or naso-jejunum tube holder of claim 10, wherein the flexible metal is aluminum.

12. The naso-gastric or naso-jejunum tube holder of claim 1, wherein the nose section has a shape and length adapted to be substantially similar to a shape and length of the patient's nose and wherein the forehead section has a length adapted to be substantially similar to a length of the patient's forehead and a width adapted to be substantially similar to a width of the patient's nose.

13. A naso-gastric or naso jejunum tube holder comprising:
   a) a conformable body having a nose section connected to a forehead section by an overlapping section, the conformable body substantially conforming to a patient's nose and forehead and extending from the patient's forehead ending at a tip of the patient's nose, wherein the nose section has a shape and length adapted to be substantially similar to a shape and length of the patient's nose and wherein the forehead section has a length adapted to be substantially similar to a length of the patient's forehead and a width adapted to be substantially similar to a width of the patient's nose;
   b) at least one means for holding at least one naso-gastric or naso-jejunum tube inserted into the patient's nose on a top of the nose section of the conformable body, the naso-gastric or naso-jejunum tube thereby substantially conforming to the top of the nose section of the conformable body along its entire length; and
   c) at least one means for holding the conformable body to a patient's forehead comprising an overlapping section connectable at varying locations along the overlapping section of the conformable body.

* * * * *